United States Patent [19]

Shimomura et al.

[11] Patent Number: 5,338,810

[45] Date of Patent: Aug. 16, 1994

[54] METHOD FOR PRODUCTION OF ACRYLATE AND ACRYLATE-CONTAINING POLYMER

[75] Inventors: Tadao Shimomura, Toyonaka; Yoshio Irie, Himeji; Hitoshi Takahashi, Himeji; Katsuhiro Kajikawa, Himeji; Jyunichi Saga, Himeji; Teruaki Fujiwara, Himeji; Takumi Hatsuda, Himeji, all of Japan

[73] Assignee: Nippon Shokubai Kagaku Kogyo Co., Ltd., Osaka, Japan

[21] Appl. No.: 27,678

[22] Filed: Mar. 8, 1993

Related U.S. Application Data

[62] Division of Ser. No. 428,350, Oct. 27, 1989, Pat. No. 5,210,298.

[30] Foreign Application Priority Data

Oct. 28, 1988 [JP]  Japan .................. 63-270773

[51] Int. Cl.$^5$ .................. C08F 2/00; C08F 130/04; C08F 120/06
[52] U.S. Cl. .................. 526/75; 526/240; 526/317.1
[58] Field of Search .................. 526/317.1, 75, 240

[56] References Cited

U.S. PATENT DOCUMENTS

4,525,527  6/1985  Takeda et al. .................. 524/831

*Primary Examiner*—Joseph L. Schofer
*Assistant Examiner*—Wu C. Cheng
*Attorney, Agent, or Firm*—Omri M. Behr; Matthew J. McDonald

[57] ABSTRACT

A method for the production of an acrylate by the neutralization reaction of acrylic acid and a basic substance, comprising sequentially (A) a step of supplying acrylic acid and said basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within said neutralization reaction system in the range of 100.1 to 110 mol % by supplying said basic substance to said neutralization reaction system, (C) a step of retaining the neutralization ratio of acrylic acid within said neutralization reaction system in the range of 100.1 to 110 mol % for a period in the range of 1 to 120 minutes thereby allowing the neutralization reaction product to age, and (D) a step of adjusting the neutralization ratio of acrylic acid within said neutralization reaction system in the range of 20 to 100 mol % by supplying acrylic acid to said neutralization reaction system, and a method for the production of an acrylate-containing polymer using the acrylate.

27 Claims, 1 Drawing Sheet

METHOD FOR PRODUCTION OF ACRYLATE AND ACRYLATE-CONTAINING POLYMER

This application is a division of application Ser. No. 07/428,350, filed Oct. 27, 1989 U.S. Pat. No. 5,210,298.

BACKGROUND OF THE INVENTION

1. Field of the Invention

This invention relates to a method for the production of an acrylate and an acrylate-containing polymer. More particularly, it relates to a method for the production of an acrylate advantageously usable for the production of an acrylate-containing polymer with a reduced residual monomer content and an acrylate-containing polymer by the use of the acrylate.

2. Description of the Prior Art

The water-soluble acrylate-containing polymers obtained by polymerizing acrylate-containing monomer components include sodium polyacrylate, acrylamide-sodium acrylate copolymer, and acrylic acid-sodium acrylate copolymer, for example. These water-soluble polymer compounds are used as flocculants for water treatment, additives for drilling mud, food additives, and viscosity enhancers, for example.

The water-swellable acrylate-containing polymers obtained by polymerizing acrylate-containing monomer components include crosslinked acrylate polymer, partially neutralized acrylic acid-crosslinked polymer and starch-acrylate graft polymer, for example. They are used as sanitary absorbents such as sanitary napkins and disposable diapers, water-retaining agents for agriculture, horticulture, and afforestation, and freshness-retaining films for foodstuffs, for example. The demand for the polymers in these fields is expected to grow further in the future.

The acrylate-containing polymer is obtained by polymerizing an acrylate or an acrylate-containing a monomer component. Various methods have been proposed for the production of such acrylate-containing polymers as in Japanese Patent Laid-Open SHO 58(1983)-108,212, Japanese Patent Laid-Open SHO 58(1983)-71,907, Japanese Patent Laid-Open SHO 53(1978)-46,389, Japanese Patent Laid-Open SHO 56(1981)-93,716, Japanese Patent Laid-Open SHO 58(1983)-49,714, Japanese Patent Laid-Open SHO 61(1986)-166,809, Japanese Patent Laid-Open SHO 62(1987)-22,811, Japanese Patent Laid-Open SHO 61(1986)-166,809, and Japanese Patent laid-Open SHO 62(1987)-22,811, for example.

The acrylates which are used as raw materials in these methods of production are generally obtained by a method which comprises adding a basic substance in a prescribed amount to an aqueous acrylic acid solution or adding acrylic acid to an aqueous solution having a prescribed amount of the basic substance dissolved therein.

Acrylate-containing polymers which are produced by using acrylates obtained by the method just mentioned generally have residual monomers remaining therein in large amounts. Particularly, in the case of a water-swellable polymer which is obtained by using a large amount of an initiator during the course of production, the produced polymer generally has an residual monomer content approximately in the range of 700 to 3,000 ppm. It goes without saying that the water-swellable acrylate-containing polymers having such large residual monomer contents as described above are undesirable as materials for a wide variety of absorbent articles represented by sanitary goods. In these applications, the polymers have the possibility of being brought into contact with human skins or even being absorbed into human bodies. When they are discarded and suffered to flow out into environments, they have the possibility of finding their way into drinking water, for example. In the circumstances, the desirability of lowering residual monomer contents in such polymers has come to command a recognition in recent years.

Generally as means of decreasing residual monomer contents in hydrophilic polymers, methods which effect a decrease in residual monomer contents of polymers by adding ammonia or amine (Japanese Patent Publication SHO 33(1958)-2,646 and Japanese Patent Laid-Open SHO 50(1975)-40,689) or adding a sulfite or a hydrogen sulfite (U.S. Pat. No. 2,960,486 and Japanese Patent Laid-Open SHO 55(1980)-135,110) to the polymers thereby inducing addition of the compounds to the residual monomers, methods which attain a decrease in the residual monomer contents of polymers by additionally using a low-temperature decomposing type or high-temperature decomposable polymerization initiator (Japanese Patent Publication SHO 50(1975)-42,280, Japanese Patent Laid-Open SHO 59(1984)-133,205, and Japanese Patent Laid-Open SHO 53(1978)-141,388) or using a redox catalyst in conjunction with an azo compound initiator (Japanese Patent Laid-Open SHO 50(1975)0-96,689 and Japanese Patent Publication SHO 47(1972)-26,430) thereby inducing polymerization of the residual monomers, and a method which accomplishes a decrease in residual monomer contents of polymers by causing the residual monomers to be decomposed by the use of a microorganism (Japanese Patent Publication SHO 60(1985)-29,523), for example, have been proposed.

Indeed the addition of ammonia, amine, sulfite, or a hydrogen sulfite is fairly effective in decreasing the residual monomer contents of the polymers, this effect is not enough when this addition is made in a small amount. This addition further entails the problem that the compound so added is toxic. The methods resorting to additional use of a polymerization initiator are not sufficiently effective in decreasing the residual monomer contents. The method relying on the action of a microorganism has the problem that the operation lacks high commercial feasibility.

An object of this invention, therefore, is to provide a novel method for the production of an acrylate and an acrylate-containing polymer.

Another object of this invention is to provide a method for production of an acrylate-containing polymer having the residual monomer content thereof decreased without a sacrifice in the substantial characteristics of the acrylate-containing polymer and a method for efficient production of an acrylate advantageously usable for the production of the polymer.

Yet another object of this invention is to provide a water-swellable acrylate-containing polymer excelling in absorption capacity, possessing only a low water-soluble content and a low residual acrylate monomer content in the cross-linked polymer, and serving advantageously as sanitary materials such as sanitary napkins and disposable diapers, as water-retaining agents for agriculture, horticulture, and afforestation, and as materials for a wide range of absorbent articles.

SUMMARY OF THE INVENTION

The objects described above are accomplished by a method for the production of an acrylate by the neutralization reaction of acrylic acid and a basic substance, comprising sequentially (A) a step of supplying acrylic acid and the basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within the neutralization reaction system in the range of 100.1 to 110 mol % by supplying the basic substance to the neutralization reaction system, (C) a step of retaining the neutralization ratio of acrylic acid within the neutralizing reaction system in the range of 100.1 to 110 mol % for a period in the range of 1 to 120 minutes thereby allowing the neutralization reaction product to age, and (D) a step of adjusting the neutralization ratio of acrylic acid within the neutralization reaction system in the range of 20 to 100 mol % by supplying acrylic acid to the neutralization reaction system.

The objects described above are also accomplished by a method for the production of an acrylate-containing polymer by the polymerization of a monomer component containing at least an acrylate obtained by the neutralization reaction of acrylic acid and a basic substance and possessed of a neutralization ratio in the range of 20 to 100 mol %, comprising sequentially (A) a step of supplying acrylic acid and the basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within the neutralization reaction system in the range of 100.1 to 110% by supplying the basic substance to the neutralization reaction system, (C) a step of retaining the neutralization ratio of acrylic acid within the neutralizing reaction system in the range of 100.1 to 110 mol % for a period in the range of 1 to 120 minutes thereby allowing the neutralization reaction product to age, and (D) a step of adjusting the neutralization ratio of acrylic acid within the neutralization reaction system in the range of 20 to 100 mol % by supplying acrylic acid to the neutralization reaction system.

The objects described above are further accomplished by an acrylate-containing polymer obtained by the polymerization of a monomer component containing at least an acrylate obtained by the neutralization reaction of acrylic acid and a basic substance and possessed of a neutralization ratio in the range of 20 to 100 mol %, comprising sequentially (A) a step of supplying acrylic acid and the basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within the neutralization reaction system in the range of 100.1 to 110 mol % by supplying the basic substance to the neutralization reaction system, (C) a step of retaining the neutralization ratio of acrylic acid within the neutralizing reaction system in the range of 100.1 to 110 mol % for a period in the range of 1 to 120 minutes thereby allowing the neutralization reaction product to age, and (D) a step of adjusting the neutralization ratio of acrylic acid within the neutralization reaction system in the range of 20 to 100 mol % by supplying acrylic acid to the neutralization reaction system.

The method for the production of an acrylate in accordance with the present invention essentially comprises specific steps. The acrylate-containing polymer which is produced by using this acrylate has the residual acrylate content thereof notably lowered without a sacrifice of the outstanding physical properties inherently owned by the acrylate-containing polymer. The water-soluble or water-swellable acrylate-containing polymer obtained by the use of the method of this invention, therefore, can be advantageously used as flocculants for water treatment, additives for drilling mud, additives for foodstuffs, absorbents or sanitary goods, water-retaining agents, and freshness-preserving films for foodstuffs, for example, without producing any adverse effect on human bodies or environments.

The method for the production of an acrylate contemplated by this invention can be worked out very easily on a commercial scale. The method for the production of an acrylate-containing polymer by the use of the acrylate as a raw material is capable for producing very efficiently the acrylate-containing polymer possessing characteristic features mentioned above.

EXPLANATION OF THE PREFERRED EMBODIMENT

Now, the present invention will be described in detail below.

The basic substance which can be used in the production of an acrylate is not specifically restricted. Any of the basic substance which are generally used for this purpose can be adopted herein. Examples of such basic substances include ammonia, organic amines, hydroxides of alkali metals, and hydroxides of alkaline earth metals. One member or a combination of two or more members selected from the group of basic substances mentioned above may be used. Among other basic substances mentioned above, hydroxides of alkali metals prove to be desirable because they are readily available and because the acrylate-containing polymers produced by the use of these hydroxides exhibit highly satisfactory qualities. Sodium hydroxide among these basic substances is particularly desirable, because ammonia and the organic amines sometimes make colored the acrylate-containing polymers thus obtained or generated odor.

In the sequential steps (A) to (D) mentioned above through which the production of an acrylate is carried out, the steps (A) and (C) are particularly important. If the operation of production misses even either of these steps (A) and (C), the objects of this invention are no longer accomplished. During the simultaneous supply of the acrylic acid and the basic substance to water for neutralization in the step (A), the neutralization ratio of the acrylic acid is constantly maintained in the range of 75 to 100 mol %. If the neutralization ratio deviates from this range, the amount of the residual monomer suffered to remain in the produced acrylate-containing polymer is unduly large. Preferably, the range is from 85 to 100 mol %. During the step (A), the temperature of the reaction system is preferable to be maintained in the range of 20° to 50° C. for the purpose of preventing the formation of impurities based on radical polymerization reaction.

The aging in the step (C) is carried out by maintaining the neutralization ratio of acrylic acid in the range of 100.1 to 110 mol %. If the neutralization ratio deviates from this range, the amount of the residual monomer suffered to remain in the produced acrylate-containing polymer is unduly large. Preferably, the range is from 100.5 to 105 mol %. The time of this aging is in the range of 1 to 120 minutes. If the aging time is less than 1 minute, the aging has no effect in lowering the residual monomer content in the produced acrylate-containing polymer. Conversely, if the aging is continued for a period exceeding 120 minutes, the excess time does not bring about any noticeable addition to the effect of aging but only entails impairment of productivity. In the step (C), the temperature of the reaction system is preferable to be maintained in the range of 20° to 50° C. for the purpose of enabling the aging to produce its effect sufficiently and, at the same time, preventing the formation of impurities based on radical polymerization reaction.

The step (D) serves the purpose of causing the neutralization ratio of acrylic acid adjusted previously in the range of 100.1 to 110 mol % for the aging in the step (C) to be readjusted in the range of 20 to 100 mol %.

The acrylate to be used in the present invention is produced by the processes of the steps (A) to (D) mentioned above, the process of the step (D) may be carried out in the vessel for neutralization reaction as used for the processes of the steps (A) to (C) or in the vessel for polymerization reaction immediately before the subsequent polymerization reaction is initiated.

The acrylate which is obtained in consequence of the sequential processes of the steps (A) to (D) has a neutralization ratio in the range of 20 to 100 mol %. If the neutralization ratio of the acrylate is less than 20 mol %, the effect of this invention is insufficient and the acrylate-containing polymer obtained by using this acrylate is such that the hydrated gel of this polymer abounds in adhesiveness possibly to the extent of impairing the facility of handling in the polymerization vessel. Conversely, if the neutralization ratio of the acrylate exceeds 100 mol %, the acrylate-containing polymer to be obtained by using this acrylate requires careful handling because of its excessive basic substance content and betrays a poor absorption capacity particularly when it is used as a water-swellable polymer.

In the production of the acrylate-containing polymer contemplated by this invention, the monomer component essentially contains the acrylate which has been obtained by the sequential processes mentioned above. It may contain other monomer (a) as occasion demands.

The monomer (a) has no particular restriction except for the sole requirement that it should be copolymerizable with the acrylate mentioned above. This monomer is preferable to possess high hydrophilicity in order that it may refrain from impairing the water absorption characteristic of the produced acrylate-containing polymer. Of the monomers (a), those of high hydrophilicity include methacrylic acid, crotonic acid, maleic acid, fumaric acid, itaconic acid, 2-acrylamide-2-methyl propanesulfonic acid, 2-(meth)acryloyl ethanesulfonic acids, 2-(meth)acryloyl propanesulfonic acids, vinyl benzenesulfonic acid, (meth)acrylamides, 2-hydroyethyl (meth)acrylates, polyethylene glycol mono(meth)acrylates, (meth)acrylonitriles, and methyl acrylate, for example. One member or a combination of two or more members selected from the group of monomers mentioned above may be used. These other monomers (a) are optionally used to suit particular purposes for which the respective produced acrylate-containing polymers are utilized. The ease with which the characteristics of this invention are manifested increases in proportion as the amount of the other monomer (a) to be used decreases. The amount of the other monomer (a) to be used, therefore, is desired to be less than 50 weight %, preferably less than 20 weight %, based on the amount of the monomer component.

In the production of the acrylate-containing polymer of this invention in a cross-linked structure, namely the water-swellable polymer, one of the following methods may be adopted to ensure efficient formation of the cross-linked structure.

(1) A method which comprises having a cross-linking monomer incorporated in advance in the monomer component thereby allowing the subsequent aqueous solution polymerization of the monomer to induce initiation of a radical polymerization reaction and consequently give rise to the cross-linked structure. The cross-linking monomer has no particular restriction except for the requirement that it should possess at least two polymerizing double bonds in the molecular unit thereof. It is preferable to exhibit a certain degree of solubility in water, possess satisfactory polymerizability with the monomer component mentioned above, assume a cross-linked structure efficiently, and give rise to a uniform cross-link distribution. The cross-linking monomers which answer the description include trimethylol propane di(meth)acrylates, pentaerythritol di(meth)acryaltes, trimethylol propane tri(meth)acrylates, pentaerythritol tri(meth)acrylates, (poly)ethylene glycol di(meth)acrylates, (poly)propylene glycol di(meth)acrylates, glycerol tri(meth)acrylates, glycerol di(meth)acrylates, N,N'-methylene bis(meth)acrylates, triallyl cyanurate, triallyl isocyanurate, triallyl amine, and triacryl phosphate, for example. One member or a combination of two or more members selected from the group of cross-linking monomers mentioned above may be used. The amount of the cross-linking monomer to be used is in the range of 0.001 to 5 mol %, preferably 0.005 to 3 mol %, based on the amount of the monomer component mentioned above. If the amount of the cross-linking agent is less than 0.001 mol %, the water-soluble content is unduly large, though the absorption ratio is large. Conversely, if this amount exceeds 5 mol %, the produced acrylate-containing polymer possesses an unduly low absorption ration.

(2) A method which comprises polymerizing the monomer component in the presence of the hydrophilic polymer compound such as starch, cellulose, or polyvinyl alcohol thereby enabling the monomer, during the course of the polymerization, to form a cross-linked structure due to graft bonding. Preferably, the hydrophilic polymer compound is used in an amount in the range of 2 to 50% by weight, based on the amount of the monomer component.

(3) A method which comprises having incorporated in advance in the monomer component a cross-linking agent possessing in the molecular unit thereof at least two groups reactive to such functional groups as acid group, hydroxyl group, amide group, etc. possessed by the monomer component thereby allowing the monomer component, during the course of polymerization and/or during the course of drying and storage, to form a cross-linked structure.

The cross-linking agents which are usable in this method include polyisocyanate compounds, polyepoxy compounds, polyamine compounds, and polyoxazoline compounds, for example. One member or a combination of two or more members selected from the group of cross-linking agents mentioned above may be used. Preferably, the amount of the cross-linking agent to be used is in the range of 0.001 to 50% by weight, preferably 0.005 to 40% by weight, based on the amount of the monomer component. If the amount of the cross-linking agent thus used is less than 0.001% by weight, the absorption ratio is high and yet the water-soluble content is unduly large. Conversely, if this amount exceeds 50% by weight, the produced acrylate-containing polymer assumes an unduly small absorption ratio.

(4) A method which comprises having a polyvalent metal compound incorporated in advance in the monomer component thereby enabling the monomer component, during the course of polymerization, to form a cross-linked structure through the phenomenon of ionic cross-linking. The polyvalent metal compounds which are usable in this method include hydroxides and salts of zinc, calcium, aluminum, and zirconium, for example. One member or a combination of two or more members selected from the group of polyvalent metal compounds mentioned above may be used.

The methods described above must be selected so as to suit the particular purposes for which the respective produced acrylate-containing polymers are utilized. Optionally, two or more of these methods may be used in combination. In the present invention, however, the formation of the cross-linked structure by the method of (1) proves to be particularly desirable in terms of the absorption capacity which the produced acrylate-containing polymer acquires.

The polymerization for the production of the polymer of this invention is accomplished by dissolving the monomer component, a polymerization initiator, and optionally a cross-linking agent in water, deaerating the resultant aqueous monomer solution with an inert gas such as nitrogen gas, and subsequently subjecting the aqueous monomer solution to polymerization using a mold frame of the type disclosed in Japanese Patent Publication SHO 48(1973-)42,466, to polymerization effected on a conveyor belt in motion as disclosed in Japanese Patent Laid-Open SHO 58(1983)-49,714, to polymerization effected in a kneader provided therein with a stirring blades adapted to divide finely the hydrated gel polymer as disclosed in Japanese Patent Laid-Open SHO 57(1982)-34,101, or to suspension polymerization as disclosed in Japanese Patent Publication SHO 59(1984)-37,003, for example.

The use of the polymerization initiator in the polymerization is not limited. The polymerization initiators which are usable herein include ammonium persulfate, potassium persulfate, hydrogen peroxide, and 2,2'-azobis(2-aminodinopropane) hydrochloride (produced by Wako Pure Chemical Industries Ltd. and marketed under product code of "V-50"), for example. The redox type initiators which are obtained by combining these polymerization initiators with such reducing agents as sodium hydrogen sulfite, L-ascorbic acid, and ferrous salts are also usable.

The acrylate-containing polymer of this invention is generally produced by way of a hydrated gel and the hydrated gel polymer has a water content generally in the range of 25 to 90% by weight, preferably 30 to 80% by weight. The amount of the polymerization initiator to be used, when the polymer is to be produced in a water soluble form, is in the range of 0.0001 to 0.5% by weight, preferably 0.002 to 0.1% by weight, based on the amount of the monomer component. When the polymer is to be produced in water-swellable form, this amount is in the range of 0.01 to 2% by weight, preferably 0.05 to 1% by weight, based on the amount of the monomer component. At times, the hydrated gel polymer obtained by the polymerization is already in a disintegrated form. In most cases, however, the hydrated gel polymer is preferable to be comminuted into a form fit for drying. The comminution is attained by a crushing action produced by the use of a meat chopper, an extruder, or a kneader, for example.

The acrylate-containing polymer of the present invention can be given the form of powder when the polymer in the aforementioned form of hydrated gel is dried and crushed. The drying devices which are usable in this invention include conductive heat transfer type driers, radiant heat transfer type driers, hot air heat transfer type driers, and induction heating driers, for example. Among other driers mentioned above, the hot air heat transfer type driers (hereinafter referred to collectively as "hot air drier") prove to be particularly desirable in terms of speed of drying. The hot air driers which are usable herein include air flow band type, rotary air flow type, vertical air flow type, parallel flow band type, air flow tunnel type, air-flow groove stirring type, fluidized bed type, air current type, and spray type driers, for example.

The acrylate-containing polymer obtained as described above has a notably decreased residual monomer content, which is not more than 0.3% by weight, for example, in the polymer which is in a water-soluble form. Particularly, in the water-swellable polymer which is required to have the residual monomer content decreased in a large measure, the residual monomer content is as low as not more than 0.05% by weight.

Now, the present invention will be described more specifically below with reference to working examples. It should be noted, however, that this invention is not limited to the examples.

EXAMPLE 1

In a distillation flask provided with a stirrer, 2,744 g of deionized water was placed. To the flask, 1,390 g of acrylic acid and 1,480 g of an aqueous 48 wt % sodium hydroxide solution were supplied over a period of 100 minutes, with the neutralization ratio of acrylic acid in the neutralization reaction system constantly controlled in the range of 90 to 95 mol %. During the supply of the reactants, the temperature of the neutralization reaction system was kept by cooling in the range of 20° to 40° C. Then, 160 g of an aqueous 48 wt % sodium hydroxide solution was supplied thereto to adjust the neutralization ratio of acrylic acid within the neutralization reaction system to 102 mol % and, at the same time, the temperature of the neutralization reaction system was adjusted to 40° C. Thereafter, the state consequently assumed was retained for 30 minutes to age the neutralization reaction product. During the course of this aging, the pH value of the neutralization reaction system was 13.9 (at 25° C.). After completion of the aging treatment, 499 g of acrylic acid was supplied to the neutralization reaction system over a period of 10 minutes. Consequently, an aqueous solution of acrylate (1) having a neutralization ratio of 75 mol % was obtained. The concentration of the acrylate (1) in the aqueous solution was 37% by weight.

EXAMPLE 2

In a distillation flask provided with a stirrer, 2,520 g of deionized water was placed. To the flask, 1,400 g of acrylic acid and 1,587 g of an aqueous 48 wt % sodium hydroxide solution were supplied over a period of 100 minutes, with the neutralization ratio of acrylic acid in the neutralization reaction system constantly controlled in the range of 98 to 100 mol %. During the supply of the reactants, the temperature of the neutralization reaction system was kept by cooling in the range of 20° to 40° C. Then, 53 g of an aqueous 48 wt % sodium hydroxide solution was supplied thereto to adjust the neutralization ratio of acrylic acid within the neutralization reaction system to 101 mol % and, at the same time, the temperature of the neutralization reaction system was adjusted to 30° C. Thereafter, the state consequently assumed was retained for 100 minutes to age the neutralization reaction product. During the course of this aging, the pH value of the neutralization reaction system was 13.4 (at 25° C.). After completion of the aging treatment, 174 g of acrylic acid was supplied to the neutralization reaction system over a period of 5 minutes. Consequently, an aqueous solution of acrylate (2) having a neutralization ratio of 90 mol % was obtained. The concentration of the acrylate (2) in the aqueous solution was 35% by weight.

EXAMPLE 3

In a distillation flask provided with a stirrer, 2,622 g of deionized water was placed. To the flask, 524 g of acrylic acid and 662 g of an aqueous 50 wt % potassium hydroxide solution were supplied over a period of 30 minutes, with the neutralization ratio of acrylic acid within the neutralization reaction system constantly controlled in the range of 80 to 82 mol %. During the supply of the reactants, the temperature of the neutralization reaction system was kept by cooling in the range of 20° to 40° C. Then, 196 g of an aqueous 50 wt % potassium hydroxide solution was supplied thereto to adjust the neutralization ratio of acrylic acid within the neutralization reaction system to 105 mol % and, at the same time, the temperature of the neutralization reaction, system was adjusted to 50° C. Thereafter, the state consequently assumed was retained for one minute to age the neutralization reaction product. During the course of this aging, the pH value of the neutralization reaction system was 14.0 (at 15° C.). After completion of the aging treatment, 1,311 g of acrylic acid was supplied to the neutralization reaction system over a period of 40 minutes. Consequently, an aqueous solution of acrylate (3) having a neutralization ratio of 30 mol % was obtained. The concentration of the acrylate (3) in the aqueous solution was 40% by weight.

EXAMPLE 4

In a distillation flask provided with a stirrer, 2,326 g of deionized water was placed. To this flask, 1,467 g of acrylic acid and 1,062 g of an aqueous 30 wt % ammonia solution were supplied over a period of 80 minutes, with the neutralization ratio of acrylic acid within the neutralization reaction system constantly controlled in the range of 90 to 95 mol %. During this supply, the temperature of the neutralization reaction system kept by cooling in the range of 20° to 40° C. Then, 116 g of an aqueous 30 wt % ammonia solution was supplied thereto to adjust the neutralization ratio of acrylic acid within the neutralization reaction system to 102 mol % and, at the same time, the temperature of the neutralization reaction system was adjusted to 40° C. Thereafter, the state consequently assumed was retained over a period of 30 minutes to age the neutralization reaction product. During the course of this aging, the pH value of the neutralization reaction system was 8.0 (at 25° C.). After completion of the aging, 31 g of acrylic acid was supplied to the neutralization reaction system over a period of two minutes. Consequently, an aqueous solution of acrylate (4) having a neutralization ratio of 100 mol % was obtained. The concentration of the acrylate (4) in the aqueous solution was 37% by weight.

CONTROL 1

In the same distillation flask as used in Example 1, 2,744 g of deionized water and 1,889 g of acrylic acid were placed. To the flask, 1,640 g of an aqueous 48 wt % sodium hydroxide solution was supplied over a period of 120 minutes. During the course of this supply, the temperature of the neutralization reaction system was kept by cooling in the range of 20° to 40° C. Consequently, an aqueous solution of an acrylate (1) for comparison having a neutralization ratio of 75 mol %. The concentration of this acrylate (1) for comparison in the aqueous solution was 37% by weight.

CONTROL 2

In the same distillation flask as used in Example 1, 2,744 g of deionized water and 1,640 g of an aqueous 48 wt % sodium hydroxide solution were placed. To the flask, 1,889 g of acrylic acid was supplied over a period of 120 minutes. During the course of this supply, the temperature of the neutralization reaction system was kept by cooling in the range of 20° to 40° C. Consequently, an aqueous solution of an acrylate (2) for comparison having a neutralization ratio of 75 mol % was obtained. The concentration of the acrylate (2) for comparison in the aqueous solution of 37% by weight.

CONTROL 3

In the same distillation flask as used in Example 1, 2,744 g of deionized water was placed. To the flask, 1,889 g of acrylic acid and 1,640 g of an aqueous 48 wt % sodium hydroxide solution were supplied over a period of 120 minutes, with the neutralization ratio of acrylic acid within the neutralization reaction system constantly controlled in the range of 70 to 80 mol %. During the course of this supply, the temperature of the neutralization reaction system was kept by cooling in the range of 20° to 40° C. Consequently, an aqueous solution of an acrylate (3) for comparison having a neutralization ratio of 75 mol % was obtained. The concentration of the acrylate (3) for comparison in the aqueous solution was 37% by weight.

CONTROL 4

In a distillation flask provided with a stirrer, 2,744 g of deionized water was placed. To the flask, 1,390 g of acrylic acid and 1,040 g of an aqueous 48 wt % sodium hydroxide solution were supplied over a period of 80 minutes, with the neutralization ratio of acrylic acid within the neutralization reaction system constantly controlled in the range of 60 to 70 mol %. During the course of this supply, the temperature of the neutralization reaction system was kept by cooling in the range of 20° to 40° C. Then, 600 g of an aqueous 48 wt % sodium hydroxide solution was supplied thereto to adjust the neutralization ratio of acrylic acid within the neutralization reaction system at 102 mol % and, at the same time, the temperature of the neutralization reaction system was adjusted to 40° C. Thereafter, the state consequently assumed was retained over a period of 30 minutes to age the neutralization reaction product. During the course of this aging, the pH of the neutralization reaction system was 13.9 (at 25° C.). After completion of the aging, 499 g of acrylic acid was supplied to the neutralization reaction system over a period of 10 minutes. Consequently, an aqueous solution of an acrylate (4) for comparison having a neutralization ratio of 75 mol % was obtained. The concentration of the acrylate (4) for comparison in the aqueous solution was 37% by weight.

CONTROL 5

In the same distillation flask as used in Example 1, 2,744 g of deionized water was placed. To the flask, 1,390 g of acrylic acid and 1,640 g of an aqueous 48 wt % sodium hydroxide solution were supplied over a period of 120 minutes, with the neutralization ratio of acrylic acid within the neutralization reaction system constantly controlled in the range of 102 to 105 mol %. During the course of this supply, the temperature of the neutralization reaction system was kept by cooling in the range of 20° to 40° C. Then, 499 g of acrylic acid was supplied thereto over a period of 10 minutes. Consequently, an aqueous solution of an acrylate (5) for comparison having a neutralization ratio of 75 mol % was obtained. The concentration of the acrylate (5) for comparison in the aqueous solution was 37% by weight.

EXAMPLE 5

A twin-arm type jacketed kneader of stainless steel possessing an inner volume of 10 liters, measuring 220 mm×240 mm in area of the opening part and 240 mm in depth, and provided with two sigma type blades 120 mm in radius of rotation was provided with a lid. In this kneader, an aqueous solution of a monomer component consisting of 5,500 g of the aqueous solution of acrylate (1) obtained in Example 1 and 3.4 g (0.05 mol %, based on the amount of the acrylate) of trimethylol propane triacrylate (the concentration of the aqueous solution 37% by weight and the neutralization ratio of the acrylate 75 mol %) was placed. Nitrogen gas was blown into the kneader to displace the internal gas entrapped inside the reaction system. Then, the two sigma type blades were set rotating at respective speeds of 67 and 56 rpm and the jacket was heated by passage therethrough of hot water at 35° C. and, at the same time, 2.8 g of ammonium persulfate and 0.7 g of sodium hydrogen sulfite were added as a polymerization initiator. The monomer component began to polymerize five minutes after the addition of the polymerization initiator. The peak temperature inside the reaction system reached 83° C. after elapse of 20 minutes following the addition of the polymerization initiator. The hydrated gel polymer at time point was in a minutely granulated form about 5 mm in particle size. Then the contents of the kneader was continuously stirred. On elapse of 60 minutes following the initiation of the polymerization, the lid was removed from the kneader and the gel formed in the kneader was removed from the kneader.

The minute granulated hydrated gel polymer thus obtained was spread on a 50-mesh metal net and dried with hot air at 180° C. for 40 minutes. The dried polymer was comminuted with a vibration mill and passed through a 20-mesh metal net to obtain an acrylate-containing polymer [1]. This polymer was tested for absorption ratio, water-soluble content, and residual monomer content. The results were as shown in Table 1.

The numerical values of absorption ratio, water-soluble content, and residual monomer content mentioned in the examples were determined by the following methods.

A. Absorption Ratio

This property was determined by uniformly placing 0.2 g of a sample polymer in a teabag-like pouch of nonwoven fabric (40 mm×150 mm), keeping the pouched sample immersed in an aqueous 0.9% NaCl solution for 30 minutes, taking weight of the pouched sample at the end of the immersion, and calculating the absorption ratio in accordance with the following formula, using the teabag-like pouch in its empty state in a blank test.

$$\text{Absorption ratio (g/g)} = \frac{\text{Weight after absorption (g)} - \text{Blank (g)}}{\text{Weight of sample polymer (g)}}$$

B. Water-Soluble Content

This magnitude was determined by dispersing 0.5 g of a sample polymer in 1,000 ml of deionized water, stirring the dispersion for 12 hours, passing the stirred dispersion through a filter paper, measuring the solid content of the filtrate, and calculating the water-soluble content in accordance with the following formula.

$$\text{Water-soluble content (\%)} = \frac{\text{Weight of filtrate (g)} \times \text{Solid content of filtrate (\%)}}{0.5 \text{ (g)}}$$

C. Residual Monomer Content

This magnitude was determined by dispersing 0.5 g of a sample polymer in 1,000 ml of distilled water, stirring the dispersion for two hours, passing the stirred dispersion through a Watman filter paper GF/F (particle retaining capacity 0.7 micron), and analyzing the filtrate by liquid chromatography.

EXAMPLES 6 AND 7 AND CONTROLS 6 TO 10

Acrylate containing polymers [2] and [3] and acrylate containing polymers [1'] to [5'] for comparison were obtained by repeating the procedure of Example 5, except that the composition of the aqueous solution of monomer component was varied as shown in Table 1. The conditions of process of polymerization reaction and the physical properties of the produced acrylate containing polymers were as shown in Table 1.

TABLE 1

|  | Example 5 | Example 6 | Example 7 | Example 8 |
|---|---|---|---|---|
| Aqueous acrylate solution | (1) | (2) | (3) | (4) |
|  | 5500 | 5500 | 4790 | 3590 |

TABLE 1-continued

| Aqueous solution of monomer component | Composition (g) | 17 wt % Aqueous meth acrylic acid solution | | | | 1910 |
|---|---|---|---|---|---|---|
| | | N,N'-methylene bisacrylamide | — | 1.6 | — | 1.4 |
| | | Trimethylol propane triacrylate | 3.4 | — | 2.0 | — |
| | | Concentration of aqueous solution (% by weight) | 37 | 35 | 40 | 30 |
| | | Neutralization ratio of acrytic acid (mol %) | 75 | 90 | 30 | 80 |
| | | Peak temperature during polymerization (°C.) | 83 | 79 | 91 | 76 |
| | | Polymerization time (min.) | 60 | 65 | 55 | 80 |
| | | Acrylate-containing polymer obtained | [1] | [2] | [3] | [4] |
| Physical properties | | Absorption ratio (g/g) | 45 | 43 | 41 | 44 |
| | | water-soluble content (% by weight) | 9 | 10 | 12 | 11 |
| | | Residual monomer content (ppm) | 400 | 400 | 410 | 390 |

| | | | Control 6 | Control 7 | Control 8 | Control 9 | Control 10 |
|---|---|---|---|---|---|---|---|
| Aqueous acrylate solution | | | Comparison (1) 5500 | Comparison (2) 5500 | Comparison (3) 5500 | Comparison (4) 5500 | Comparison (5) 5500 |
| Aqueous solution of monomer component | Composition (g) | 17 wt % Aqueous meth acrylic acid solution | | | | | |
| | | N,N'-methylene bisacrylamide Trimethylol propane triacrylate | 1.8 | 1.8 | 1.8 | 1.8 | 1.8 |
| | | Concentration of aqueous solution (% by weight) | 37 | 37 | 37 | 37 | 37 |
| | | Neutralization ratio of acrytic acid (mol %) | 75 | 75 | 75 | 75 | 75 |
| | | Peak temperature during polymerization (°C.) | 83 | 83 | 83 | 80 | 85 |
| | | Polymerization time (min.) | 60 | 60 | 60 | 65 | 60 |
| | | Acrylate-containing polymer obtained | Comparison [1'] | Comparison [2'] | Comparison [3'] | Comparison [4'] | Comparison [5'] |
| Physical properties | | Absorption ratio (g/g) | 45 | 45 | 45 | 43 | 45 |
| | | water-soluble content (% by weight) | 10 | 10 | 10 | 10 | 10 |
| | | Residual monomer content (ppm) | 750 | 760 | 710 | 650 | 760 |

EXAMPLE 8

In the same kneader as used in Example 5, the aqueous solution of a monomer component consisting of 3,590 g of the aqueous solution of acrylate (4) obtained in Example 4, 1,910 g of an aqueous 17 wt % methacrylic acid solution, and 1.4 g of N,N'-methylene bisacrylamide (concentration of the aqueous solution 30% by weight was placed. Nitrogen gas was blown into the kneader to displace the internal gas entrapped in the reaction system. Then, the two sigma type blades were set rotating at respective speeds of 67 and 56 rpm, the jacket was heated by passing therethrough hot water at 35° C. and, at the same time, 1.0 g of ammonium persulfate and 0.25 g of sodium hydrogen sulfite were added as a polymerization initiator. The peak temperature inside the reaction system reached 76° C. after elapse of 40 minutes following the addition of the polymerization initiator. At this time, the hydrated gel polymer was in a minutely granulated form about 5 mm in particle size. The stirring of the polymer was further continued. On elapse of 80 minutes following the initiation of the polymerization, the lid was removed from the kneader and the gel was removed from the kneader.

The minutely granulated hydrated gel polymer consequently obtained was treated in the same manner as in Example 5, to produce an acrylate-containing polymer (4).

EXAMPLE 9

In a distillation flask provided with a stirrer, 1,944 g of deionized water was placed. To the flask, 1,390 g of acrylic acid and 1,480 g of an aqueous 48 wt % sodium hydroxide solution were supplied over a period of 100 minutes, with the neutralization ratio of acrylic acid within the neutralization reaction system constantly controlled in the range of 90 to 95 mol %. During the course of this supply, the temperature of the neutralization reaction system was kept by cooling in the range of 20° to 40° C. Then, 160 g of an aqueous 48 wt % sodium hydroxide solution was supplied thereto to adjust the neutralization ratio of acrylic acid within the neutralization reaction system to 102 mol % and, at the same time, the temperature of the neutralization reaction system was adjusted to 40° C. Thereafter, the state consequently assumed was retained for 30 the minutes to age the neutralization reaction product. During course of this aging, the pH value of the neutralization reaction system was 13.9 (at 25° C). After completion of the aging, 28 g of acrylic acid was supplied to the neutralization reaction system over a period of one minute. Consequently, an aqueous solution of an acrylate (5) having a neutralization ratio of 100 mol % was obtained. The concentration of the acrylate (5) in this aqueous solution was 37% by weight.

Figure 1:
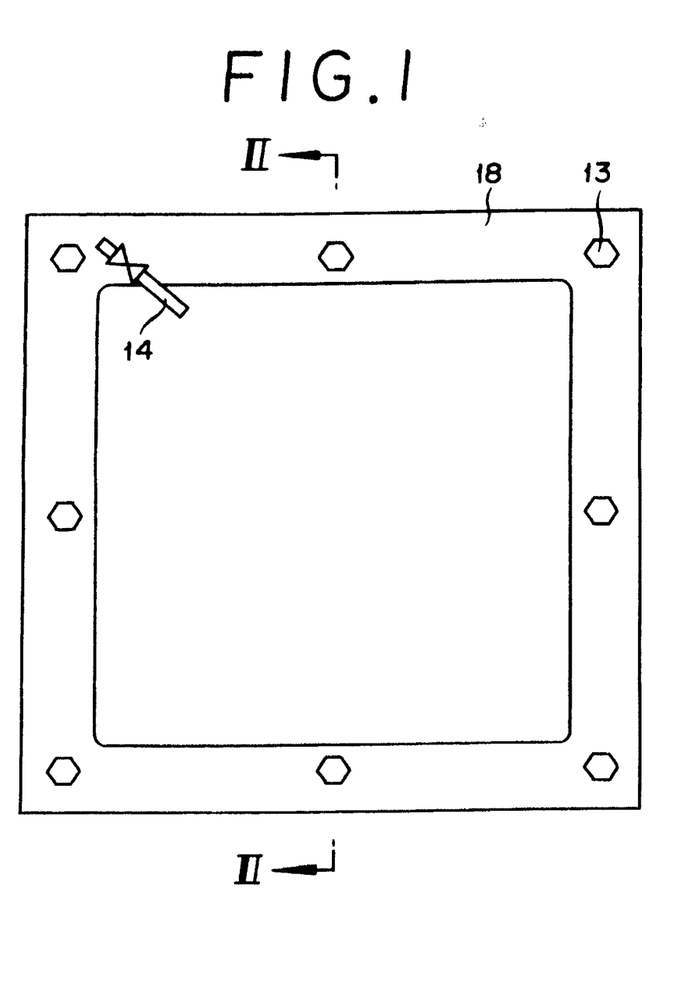
FIG. 1 is a schematic front view of a polymerization apparatus used in Example 9 and Control 11 cited herein.
Figure 2:
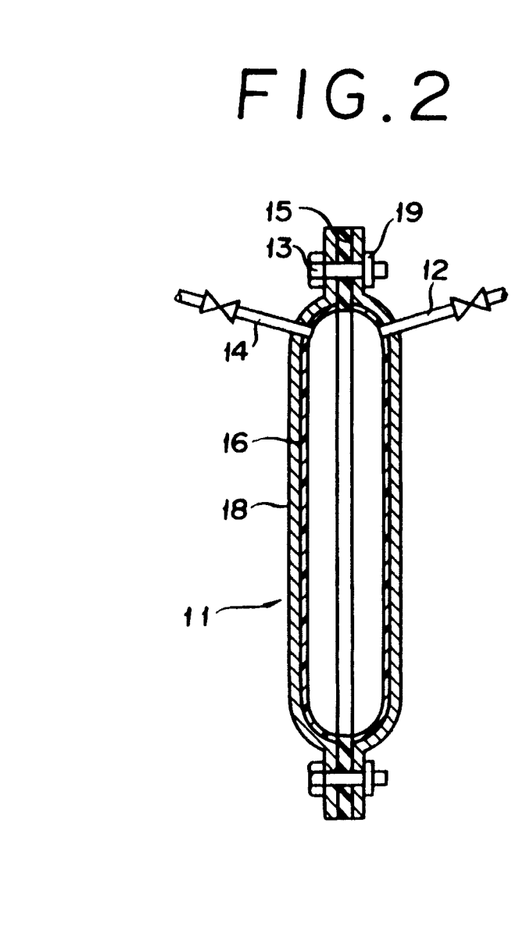
FIG. 2 is a cross section taken through FIG. 1 along the line II—II.

In a polymerization device (1.6 liters in inner volume, 230 mm in length, 230 mm in breadth, and 30 mm in width) configured as illustrated in FIG. 1 and FIG. 2 by interposing a rubber packing 15 between two stainless steel sheets 18 lined with a fluorine resin coating 16 and sealing the edges of the stainless steel sheets 18 and the rubber packing 15 by fastening them with bolts 13 and nuts 19, 2,000 g of an aqueous 37 wt % acrylate solution (5) deaerated in advance with nitrogen gas, 0.08 g of ammonium persulfate, and 0.04 g of sodium hydrogen sulfite were introduced via a raw material inlet 12, with the entrapped air discharged via an air outlet 14. This polymerization device was placed in a water bath provided with a stirrer and a temperature controller. By keeping the temperature of the water bath at 30° C., the monomer component was polymerized and the heat of reaction was eliminated. After elapse of five hours following the initiation of the polymerization, the hydrated gel polymer consequently formed in the polymerization device was removed. The polymer was cut into ribbons with a meat chopper, spread on a 50-mesh metal net, and dried with hot air at 180° C. for 60 minutes. The dried ribbons of polymer were comminuted with a vibration mill, passed through a 20-mesh metal net to obtain an acrylate-containing polymer [5].

The acrylate containing polymer [5] was tested for residual monomer content by the bromine addition method. The aqueous solution prepared by dissolving 0.2 g of the polymer in 100 g of deionized water was tested for viscosity at 25° C. by the use of a Brookfield viscosimeter. The results were as shown in Table 2.

CONTROL 11

In the same distillation flask as used in Example 1, 1,944 g of deionized water and 1,418 g of acrylic acid were placed. To the flask, 1,640 g of an aqueous 48 wt % sodium hydroxide solution were supplied over a period of 120 minutes. During the course of this supply, the temperature of the neutralization system was kept by cooling in the range of 20° to 40° C. Consequently, an aqueous solution of an acrylate (6) for comparison having a neutralization ratio of 100 mol % was obtained. The concentration of the acrylate (6) for comparison in the aqueous solution was 37% by weight.

An acrylate-containing polymer [6'] for comparison was obtained by repeating the procedure of Example 9, except that the acrylate (6) for comparison was used instead. This acrylate-containing polymer [6'] for comparison was tested for physical properties in the same manner as in Example 9. The results were as shown in Table 2.

TABLE 2

|           | Residual monomer content (ppm) | Viscosity of aqueous solution (cp) |
| --------- | ------------------------------ | ---------------------------------- |
| Example 9 | 2,100                          | 580                                |
| Control 11 | 2,600                         | 580                                |

What is claimed is:

1. A method for the production of an acrylate-containing polymer having low residual monomer levels by the polymerization of a monomer component containing at least a monomeric acrylate produced by a series of neutralization reactions of acrylic acid and a basic substance, said series of neutralization reactions comprising sequentially (A) a step of supplying acrylic acid and said basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within said neutralization reaction system in the range of 100.1 to 110 mol % by supplying said basic substance to said neutralization reaction system, (C) a step of retaining the neutralization ratio of acrylic acid within said neutralization reaction system in the range of 100.1 to 110 mol % for a period in the range of 1 to 120 minutes thereby allowing the neutralization reaction product to age, and (D) a step of adjusting the neutralization reaction system in the range of 20 to 100 mol % by supplying acrylic acid to said neutralization reaction system, whereby said monomer component is formed, thereafter polymerizing said monomer component by the series of steps, comprising sequentially (E) deaerating the aqueous monomer solution with an inert gas, (F) adding a polymerization initiator to said aqueous monomer solution, and (G) subjecting the resultant mixture to polymerization conditions.

2. A method according to claim 1, wherein the acrylate content of said monomer component is in the range of 50 to 100% by weight.

3. A method according to claim 1, wherein said monomer component further incorporates therein a monomer capable of cross-linking.

4. A method according to claim 3, wherein said acrylate-containing polymer possesses a cross-linked structure.

5. A method according to claim 3, wherein said monomer capable of cross-linking is used in an amount in the range of 0.001 to 5% mol %, based on the amount of said monomer component.

6. A method according to claim 1, wherein said basic substance is the hydroxide of an alkali metal.

7. A method according to claim 1, wherein said neutralization ratio of acrylic acid within said neutralization reaction system in the step (A) is constantly in the range of 85 to 100 mol %.

8. A method according to claim 1, wherein said neutralization reaction in the step (A) is carrier out at a temperature in the range of 20° to 50° C.

9. A method according to claim 1, wherein said neutralization ratio of acrylic acid within said neutralization reaction system in the step (C) is in the range of 100.5 to 105 mol %.

10. A method according to claim 1, wherein said neutralization reaction in the step (C) is carried out at a temperature in the range of 20° to 50° C.

11. An acrylate-containing polymer obtained by the polymerization of a monomer component containing at least at acrylate produced by the neutralization reaction of acrylic acid and a basic substance, comprising sequentially (A) a step of supplying acrylic acid and said basic substance to water thereby subjecting them to a neutralization reaction while constantly retaining the neutralization ratio of acrylic acid within the neutralization reaction system in the range of 75 to 100 mol %, (B) a step of adjusting the neutralization ratio of acrylic acid within said neutralization reaction system in the range of 100.1 to 110 mol % by supplying said basic substance to said neutralization reaction system, (C) a step of retaining the neutralization ratio of acrylic acid within said neutralizing reaction system in the range of 100.1 to 110 mol % for a period in the range of 1 to 120 minutes thereby allowing the neutralization reaction product of age, and (D) a step of adjusting the neutralization ratio of acrylic acid within said neutralization reaction system in the range of 20 to 100 mol % by supplying acrylic acid to said neutralization reaction system.

12. A polymer according to claim 11, wherein the acrylate content of said monomer component is in the range of 50 to 100% by weight.

13. A polymer according to claim 12, wherein said acrylate-containing polymer possesses a cross-linked structure.

14. A polymer according to claim 13, wherein said monomer component incorporates therein a monomer capable of cross-linking.

15. A polymer according to claim 14, wherein said monomer capable of cross-linking is used in an amount in the range of 0.001 to 5 mol %, based on the amount of said monomer component.

16. A polymer according to claim 11, wherein said basic substance is the hydroxide of an alkali metal.

17. A polymer according to claim 11, wherein said neutralization ratio of acrylic acid within said neutralization reaction system in the step (A) is constantly in the range of 85 to 100 mol %.

18. A polymer according to claim 11, wherein said neutralization reaction in the step (A) is carried out at a temperature in the range of 20° to 50° C.

19. A polymer according to claim 11, wherein said neutralization ratio of acrylic acid within said neutralization reaction system in the step (C) is in the range of 100.5 to 105 mol %.

20. A polymer according to claim 11, wherein said neutralization reaction in the step (C) is carried out at a temperature in the range of 20° to 50° C.

21. The method of claim 1 wherein subjecting the mixture to polymerization conditions is performed in a polymerization device.

22. The method of claim 21 wherein the polymerization device is a mold frame.

23. The method of claim 21 wherein the polymerization device is a conveyor belt.

24. The method of claim 21 wherein the polymerization device is a kneader.

25. The method of claim 1 wherein subjecting the mixture to polymerization conditions is performed by suspension polymerization.

26. The method of claim 1 wherein the aqueous monomer solution is diluted with water prior to deaerating.

27. A method for the production of an acrylate-containing polymer having low residual monomer levels by the polymerization of a monomer component containing at least a monomeric acrylate produced by a series of neutralization reactions of acrylic acid and a basic substance, said series of neutralization reactions comprising sequentially (A) a step of supplying acrylic acid and said basic substance to water thereby subjecting them to a neutralization reaction while constantly retaining the neutralization ratio of acrylic acid within the neutralization reaction system in the range of 75 to 100 mol %.

(B) a step of adjusting the neutralization ratio of acrylic acid within said neutralization reaction system in the range of 100.0 to 110 mol % by supplying said basic substance to said neutralization reaction system, (C) a step of retaining the neutralization ratio of acrylic acid within said neutralization reaction system in the range of 100.1 to 110 mol % for a period in the range of 1 to 120 minutes thereby allowing the neutralization reaction product to age, and (D) a step of adjusting the neutralization reaction system in the range of 20 to 100 mol % by supplying acrylic acid to said neutralization reaction system, whereby said monomer component is formed, thereafter polymerizing said monomer component by the series of steps, comprising sequentially (E) adding a polymerization initiator to said aqueous monomer solution, (F) deaerating the aqueous monomer solution with inert gas, and (G) subjecting the resultant mixture to polymerization conditions.

* * * * *